United States Patent
Kinoshita et al.

(10) Patent No.: US 6,187,932 B1
(45) Date of Patent: Feb. 13, 2001

(54) SIMPLE PROCESS FOR PRODUCING HIGH QUALITY CAPTOPRIL

(75) Inventors: Koichi Kinoshita, Takasago; Fumihiko Kano, Himeji; Takahiro Okubo, Kobe; Yasuyoshi Ueda, Himeji, all of (JP)

(73) Assignee: Kaneka Corporation, Osaka (JP)

( * ) Notice: Under 35 U.S.C. 154(b), the term of this patent shall be extended for 0 days.

(21) Appl. No.: 09/077,747

(22) PCT Filed: Oct. 13, 1997

(86) PCT No.: PCT/JP97/03655

§ 371 Date: Aug. 3, 1998

§ 102(e) Date: Aug. 3, 1998

(87) PCT Pub. No.: WO98/16509

PCT Pub. Date: Apr. 23, 1998

(30) Foreign Application Priority Data

Oct. 11, 1996 (JP) .................................................. 8-289340

(51) Int. Cl.⁷ .................................................. C07D 207/12
(52) U.S. Cl. .................................................. 548/533
(58) Field of Search .................................................. 548/533

(56) References Cited

U.S. PATENT DOCUMENTS

| 4,297,282 | * | 10/1981 | Ohashi et al. | 260/326.2 |
|---|---|---|---|---|
| 5,276,207 | * | 1/1994 | Schneider et al. | 548/533 |
| 5,387,697 | * | 2/1995 | Hen | 548/533 |
| 5,473,081 | * | 12/1995 | Kobayashi et al. | 548/533 |

FOREIGN PATENT DOCUMENTS

| 5-221966 | 8/1993 | (JP) . |
|---|---|---|
| WO97/12858 | 4/1997 | (WO) . |

OTHER PUBLICATIONS

Jerry March, Advanced Organic Chemistry, 4th Ed., pp. 378–379, 1992.*
E. Emmet Reid, Organic Chemistry of Bivalent Sulfur, vol. IV, pp. 31–35, 1962.*

R.J. Boyce et al, Total Synthesis of Thiangazole, a Novel Naturally Occurring HIV–1 Inhibitor from Polygangium sp, Tetrahedron (incl. Tetrahedron Reports), Vol. 51, No. 26, 1995, pp. 7321–7330, XP002128001.

L. Bauer et al, The Synthesis of (Hydroxylamino)alkyl Mercaptans, Journal of Organic Chemistry, Vol. 30, 1965, pp. 4298–4303, XP002129002.

* cited by examiner

*Primary Examiner*—Johann Richter
*Assistant Examiner*—Jane C. Oswecki
(74) *Attorney, Agent, or Firm*—Pollock, Vande Sande & Amernick

(57) ABSTRACT

A process for producing captopril of the following formula (1) comprising subjecting a substrate compound of the following general formula (2) to a hydrolysis reaction in aqueous medium to remove the RCO group and isolating the product compound, said hydrolysis reaction in aqueous medium being conducted in the presence of a strong acid at pH not over 1 and a reaction temperature not below 40° C.

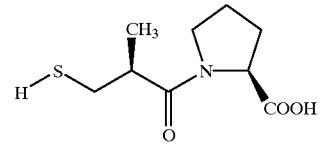

(1)

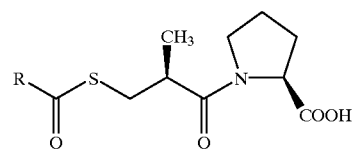

(2)

25 Claims, No Drawings

SIMPLE PROCESS FOR PRODUCING HIGH QUALITY CAPTOPRIL

This application is 371 of PCT/JP97/03655 filed Oct. 13, 1997.

FIELD OF THE INVENTION

The present invention relates to a process for producing captopril of formula (1)

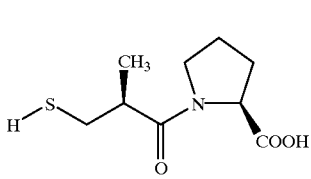

(1)

from a substrate compound of the general formula (2)

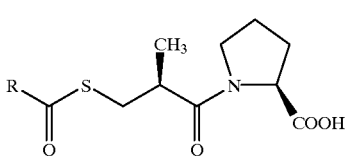

(2)

wherein R represents alkyl or alkoxy. Captopril, which has the above formula (1), is an antihypertensive compound having high angiotensin-converting enzyme inhibitory activity (e.g. Biochemistry, 16, 5487, 1977).

BACKGROUND ART

As a method of synthesizing captopril of the above formula (1) from a substrate compound of the above general formula (2) [hereinafter referred to as substrate compound (2)], experimental examples of the reaction under basic conditions using an alkali metal hydroxide or the like have heretofore been reported (e.g. U.S. Pat. No. 4,105,776 and Japanese Kokai Publication Hei-3-169856 and Hei-5-221966).

As can be understood from the following reaction schema, any reaction under such basic conditions is a stoichiometric reaction in which at least 3 moles of an alkali metal hydroxide, for instance, may be consumed for each mole of substrate compound (2) (Japanese Kokai Publication Hei-3-169856).

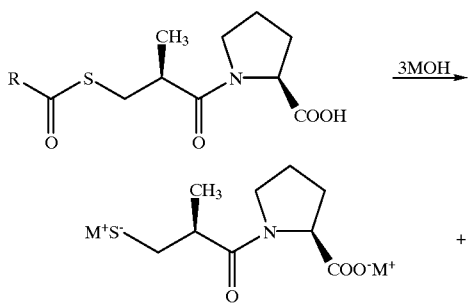

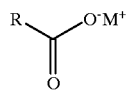

wherein R is as defined hereinbefore; M represents an alkali metal ion such as Na.

The above reaction is disadvantageous in that it gives rise to a disulfide of the following formula (7) as a byproduct contaminating the product captopril.

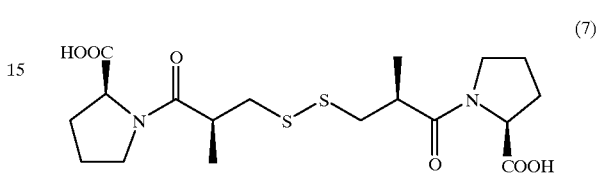

(7)

Once the disulfide of formula (7) is by-produced, it takes much time and labor to remove the byproduct [Chemical Pharmaceutical Bulletin, 30 (9), 3139–3146, 1982; Chinese Patent 1034920A].

It is known that the by-production of the disulfide of formula (7) and other impurities is chiefly attributable to oxidation reactions involving molecular oxygen [Shigeru Ohba: Organosulfur Chemistry, Reaction Mechanisms, Kagaku Dojin).

For suppressing by-production of said disulfide of formula (7), the production of captopril from substrate compound (2) is generally carried out in an inert atmosphere such as nitrogen gas, helium gas, argon gas, or hydrogen gas [e.g. Japanese Kokai Publication Hei-5-221966].

However, the use of such an inert atmosphere for the reaction is a mere negative contrivance designed to prevent infiltration of oxygen and once oxygen has found its way into the reaction system, the by-production of said disulfide of formula (7) can hardly be inhibited.

It is difficult to completely eliminate oxygen and any residual oxygen has a serious adverse effect. For example, in the reaction giving rise to said byproduct disulfide of formula (7) from captopril and molecular oxygen, one mole of oxygen may consume as many as 4 moles of captopril as shown below (Japanese Kokai Publication Hei-3-169856).

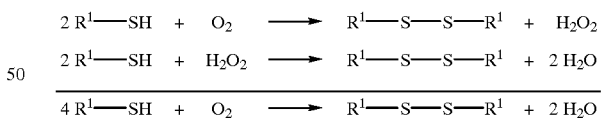

In the above reaction schema, $R^1$ represents a captopril residue of the following formula.

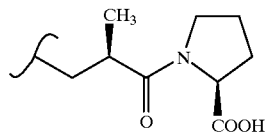

Furthermore, the captopril obtained by the above reaction may contain N-(α-methyl-β-(β-methyl-β-hydroxycarbonyl) ethylthiopropionyl)-L-proline of the following formula (8) as an onerous impurity.

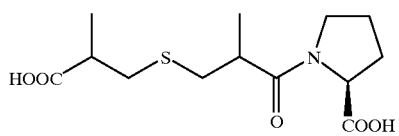

(8)

Thus, N-(α-methyl-β-(β-methyl-β-hydroxycarbonyl) ethylthiopropionyl)-L-proline of formula (8) can hardly be removed by a purification procedure and its elimination calls for a great deal of effort (Japanese Kokai Publication Hei-5-221966).

The investigation made by the inventors of the present invention (as disclosed in Japanese Patent Application Hei-7-286886) revealed that this N-(α-methyl-β-(β-methyl-β-hydroxycarbonyl)ethylthiopropionyl)-L-proline of formula (8) is derived from the compound of the following general formula (3) and/or the compound of the following formula (4) which are/is present concomitantly with said substrate compound (2) in the reaction system for synthesis of captopril.

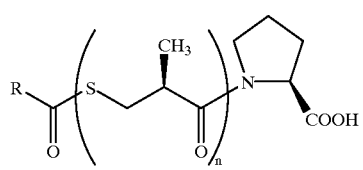

(3)

wherein R is as defined hereinbefore; n represents an integer of 2 to 4.

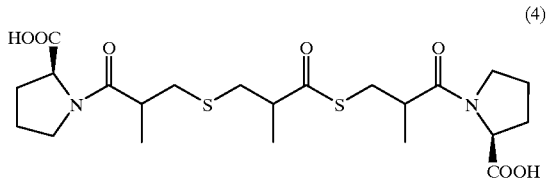

(4)

Therefore, it is important to inhibit or suppress the conversion of the compound of general formula (3) [hereinafter referred to as compound (3)] and/or the compound of formula (4) [hereinafter referred to as compound (4)] to said N-(α-methyl-β-(β-methyl-β-hydroxycarbonyl) ethylthiopropionyl)-L-proline of general formula (8).

The above compound (3) and/or compound (4) is readily by-produced in the course of the synthesis of said substrate compound (2) by, for example, the Schotten-Baumann reaction between an acid halide of the following general formula (5) and L-proline of the following formula (6) under basic conditions.

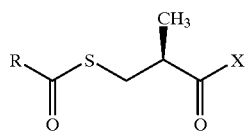

(5)

wherein R is as defined hereinbefore; X represents halogen.

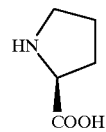

(6)

It has been discovered that in the course of cleavage of RCO under basic conditions, the byproduct compound is converted to the above-mentioned compound of formula (8).

SUMMARY OF THE INVENTION

In view of the above state of the art, the present invention has for its object to provide a highly convenient process for producing high-quality captopril in high yield and at low cost, which is conducive to minimized by-production of impurities which are hardly removed by purification.

The present invention, therefore, is directed to a process for producing captopril which comprises subjecting substrate compound (2) to hydrolysis reaction in aqueous medium to eliminate RCO group and isolating, said hydrolysis reaction in aqueous medium being conducted in the presence of a strong acid at pH not over 1 and a temperature not below 40° C.

The present invention is now described in detail.

DETAILED DESCRIPTION OF THE INVENTION

The substrate compound (2) for use in the present invention can be prepared by any of the processes described in U.S. Pat. No. 4,105,776, Japanese Kokai Publication Hei-4-305565, and other literature.

When the substrate compound (2) is to be produced by the Schotten-Baumann reaction of an acid halide of general formula (5) with L-proline of formula (6) under basic conditions, the amount of said compounds (3) and (4), which are precursors of N-(α-methyl-β-(β-methyl-β-hydroxycarbonyl)ethylthiopropionyl)-L-proline of formula (8), is preferably as small as possible.

The substrate compound (2) that contains small amounts of said compound (3) and/or compound (4) is described in Japanese Patent Application Hei-7-286886 and can be advantageously provided by the following reaction procedure (A) or (B) and/or the following purification procedure (C) or (D) as followed either alone or in a suitable combination.

(A) The above-mentioned Schotten-Baumann reaction of an acid halide of general formula (5) with L-proline of formula (6) in a basic aqueous medium in the presence of a deacidifying condensing agent is conducted at pH 7–10 and a reaction temperature of not over 10° C. to thereby suppress by-production of said compound (3) and/or compound (4).

(B) The Schotten-Baumann reaction of an acid halide of general formula (5) with L-proline of formula (6) in a basic aqueous medium in the presence of a deacidifying condensing agent is conducted using potassium hydrogen carbonate as the deacidifying condensing agent preferably at a reaction temperature of not over 10° C. to thereby suppress by-production of said compound (3) and/or compound (4).

The above reaction procedure (A) is advantageous in that the reaction under weakly alkaline conditions and at a low temperature is highly conducive to inhibition of by-production of said compound (3) and/or compound (4). The reaction procedure (B) is advantageous in that since potassium hydrogen carbonate is used as the deacidifying condensing agent, the desired weakly alkaline conditions can be easily maintained without the need to control the reaction pH by any specific means, with the result that the by-production of said compound (3) and/or compound (4) can be effectively inhibited.

To prevent contamination of captopril with said byproduct compounds (3) and (4), (C) the substrate compound (2) is caused to crystallize out from the aqueous medium containing it at a temperature of 35–100° C. and under acidic conditions, preferably at pH 1–4, to thereby remove the contaminant compound (3) and/or compound (4), and (D) the aqueous medium containing said substrate compound (2) is treated with activated carbon at pH not over 12, preferably at pH 2–12, to thereby remove the contaminant compound (3) and/or compound (4).

The purification procedure (C) mentioned above is advantageous in that the crystallization from an aqueous medium at an elevated temperature is highly effective in removing said concomitant compound (3) and/or compound (4). The purification procedure (D) mentioned above is advantageous in that the treatment with activated carbon in aqueous medium is highly effective in removing the concomitant compound (3) and/or compound (4).

The aqueous medium mentioned above is water essentially not containing an organic solvent. The aqueous medium thus includes water and water containing an organic solvent in an amount not contrary to the object of the invention. The same holds true for all the aqueous media mentioned in the following disclosure.

Referring to the above substrate compound (2), R represents alkyl or alkoxy, and is generally a lower alkyl group or a lower alkoxy group. Particularly preferred is methyl.

In accordance with the present invention, the above substrate compound (2) is subjected to hydrolysis reaction in an aqueous medium in the presence of a strong acid at pH not over 1 and a temperature not below 40° C., whereby the RCO group is cleaved to yield captopril.

The hydrolysis reaction in aqueous medium proceeds as shown below.

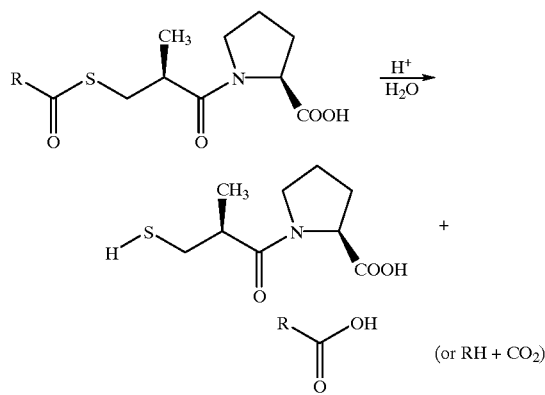

In the above reaction schema, R is as defined hereinbefore.

The strong acid that can be used for the above hydrolysis reaction in aqueous medium includes organic acids such as p-toluenesulfonic acid, methanesulfonic acid, trihaloacetic acids, etc. and inorganic acids such as hydrohalogenic acids, phosphoric acid, sulfuric acid, etc., although hydrochloric acid is particularly advantageous.

There is no particular limitation on the amount of strong acid relative to said substrate compound (2) but generally 0.1 or more molar equivalent is used. Depending on the reaction temperature, the strong acid is generally used in a proportion of about 0.2–2 molar equivalents.

The reaction temperature for said hydrolysis reaction in aqueous medium is not below about 40° C. and preferably not below about 50° C. Thus, the reaction is generally carried out at about 50–100° C. The reaction pH is not over about 1 and preferably in the neighborhood of about 0 or below.

Generally speaking, the lower the reaction temperature is, preferably the larger is the proportion of the strong acid. When the reaction temperature is high, the reaction proceeds readily even in the small amount of strong acid.

The reaction temperature and reaction pH are important parameters for enhancing the solubility of substrate compound (2) to make the main reaction proceed smoothly and inhibit formation of byproducts, thus providing for convenient production of said captopril of good quality in high yield. When the reaction temperature is too low or the reaction pH is too high, the main reaction does not proceed uneventfully so that the yield of captopril can hardly be increased.

Referring, further, to said hydrolysis reaction in aqueous medium, strongly acidic conditions contribute to suppressing the by-production of said disulfide owing to the oxidation of the product captopril by dissolved oxygen and to suppression of by-production of said N-(α-methyl-β-(β-methyl-β-hydroxycarbonyl)ethylthiopropionyl)-L-proline of formula (8), which can hardly be removed by subsequent purification, from said compounds (3) and (4) which may be concomitantly present with the substrate compound (2).

The aqueous medium for use in the present invention is preferably an aqueous solution. There is no merit in the use of an organic solvent. However, if necessary, the hydrolysis reaction may be carried out in water containing an organic solvent. The use of an aqueous solution not only improves the operability and safety of the production process itself but contributes much to product safety because of the freedom from contamination of captopril with organic solvents which may not be benign to human health.

The step for isolating captopril is now described.

This isolation of captopril is effected by crystallization, solvent extraction, or solvent extraction and subsequent crystallization.

The above-mentioned crystallization is carried out, following the above reaction, at pH not over 3 and preferably in the pH region of about 1 to 2. Thus, the reaction mixture after completion of the reaction can be subjected to crystallization, either as it is or after concentration under reduced pressure, or after having been adjusted to a pH of not less than 4 to 5 and then conducting acidification again.

The crystallization is carried out at a temperature not over about 50° C. and preferably at about 15 to 45° C. To obtain high-quality crystals with satisfactory crystal property, it is most advantageous to perform crystallization at about 40±5° C. usually, it is preferable to complete crystallization at a final temperature of not over about 5° C.

In order to provide for satisfactory growth of said high-quality captopril crystals having good crystal property in the above crystallization step, it is preferable to gradually lower the solubility of captopril or see to it that no supersaturation will take place. For this purpose, one may advantageously employ a crystallization schema comprising gradual cooling under acidic conditions or a schema comprising gradual acidification at the above-mentioned crystallization temperature. It is also a preferred procedure to add seed crystals for assisting in crystal growth and avoiding occurance of supersaturation.

In the present invention, where necessary, an inorganic salt of the common variety can be added to the system for the purpose of bringing its inorganic salt concentration of the aqueous medium to saturation to thereby lower the solubility of captopril and increase the yield of captopril. Among such inorganic salts, sodium chloride is particularly preferred for its high salting-out effect. In addition, the loss of the product can be minimized by recycling the mother liquor and/or washing solution containing said captopril.

In the present invention, the reaction mixture can be treated with a base prior to crystallization or solvent extraction in order to convert other trace contaminants into impurities which can be easily removed by crystallization. This base treatment is carried out at pH not below 12, preferably not below 13, generally at a temperature of about 0–50° C. for 1 minute to several hours. By way of illustration, it is sufficient to carry out this treatment at pH 13 to 14 and 25° C. for 1 hour. Thereafter, crystallization is carried out under the acidic conditions mentioned above.

The proper combination of species of said acid and base for use in the course of production of captopril through its isolation contributes to formation of a safe inorganic salt which is easy in effluent disposal, an increased crystallization yield of captopril due to a salting-out effect, and the ease of handling. The preferred acid is hydrochloric acid. The base is preferably alkali metal hydroxides and alkali metal carbonates, etc. The more preferred base is an alkali metal hydroxide, with sodium hydroxide being particularly useful.

In the present invention, the captopril crystals which have separated out are recovered by the routine crystal crop harvesting procedure such as centrifugation or pressure-filtration and then rinsed with water, preferably cold water.

As an alternative, the product captopril can be isolated by solvent extraction or solvent extraction and subsequent crystallization. The solvent extraction mentioned above is carried out using an organic solvent, preferably an acetic acid ester, under acidic conditions not over pH 4.5, preferably not over pH 3. Captopril is optionally crystallized from the extract.

The acetic acid ester mentioned above includes alkyl esters of 1–4 carbon atoms and is preferably ethyl acetate, isopropyl acetate, or tert-butyl acetate. Particularly preferred is tert-butyl acetate. For an increased crystallization yield, a hydrocarbon compound, preferably n-hexane or methylcyclohexane, can be added.

The prevention of oxidation can be made more thoroughly by carrying out the process of the invention in a non-oxidizing inert atmosphere. There is no particular limitation on the inert atmosphere that can be used and any of nitrogen gas, helium gas, argon gas, hydrogen gas, etc. can be utilized.

BEST MODES FOR CARRYING OUT THE INVENTION

The following examples are intended to illustrate the present invention in further detail and should by no means be construed as defining the scope of the invention.

In the following examples, N-(D-α-methyl-β-acetylthiopropionyl)-L-proline (R=methyl) was used as substrate compound (2).

EXAMPLE 1

Preparation of N-(D-α-methyl-β-acetylthiopropionyl)-L-proline

To 255 g of deionized water was added 57.0 g (0.495 mole) of L-proline and the mixture was cooled to about 5° C. Under stirring, 30 wt. % aqueous solution of NaOH was added slowly dropwise to adjust the mixture to pH 11.3 at about 0–3° C. Then, with the mixture being maintained at pH 11.0 to 11.5 in a nitrogen atmosphere, 87.6 g (0.485 mole) of D-α-methyl-β-acetylthiopropionyl chloride was added dropwise over about 1 hour at 2–5° C. with an agitation power of about 1.5 KW/m$^3$. After completion of dropwise addition, the ripening reaction was carried out under the same conditions for about 2 hours. This reaction mixture was adjusted to pH 7 by dropwise addition of 35 wt. % aqueous solution of HCl in a nitrogen atmosphere at about 1° C. Then, at an internal temperature of about 20° C. and under strong agitation, the reaction mixture was acidified with 35 wt. % aqueous solution of HCl to cause crystallization in a nitrogen atmosphere. Thirty five wt. % aqueous solution of HCl was added rapidly down to pH 5 and, thereafter, dropwise at a decreasing rate of about 0.2 pH unit at 15-minute intervals down to pH 3 so as to cause crystallization gradually. Then, the dropping rate of 35 wt. % aqueous solution of HCl was gradually increased until a final pH value of 1.5 had been attained. The system was cooled gradually down to about 10° C. and mild stirring was continued for about 2 hours. The crystal crop was harvested by filtration, drained well, rinsed with about 180 ml of cold water, and sufficiently drained to provide 131.7 g of wet crystals (water content 15.0%) of N-(D-α-methyl-β-acetylthiopropionyl)-L-proline (yield 89%; compound (3) (n=2) content=3.7 wt. % and compound (4) content=0.1 wt. %).

EXAMPLE 2

Preparation of N-(D-α-methyl-β-acetylthiopropionyl)-L-proline with Low Contents of Compound (3) and Compound (4)

To 85 g of deionized water was added 19.0 g (0.165 mole) of L-proline and the mixture was cooled to about 5° C. Under stirring, 30 wt. % aqueous solution of NaOH was added slowly dropwise to adjust the mixture to pH 7.6 at about 0–3° C. Then, with the mixture being maintained at pH 7.4 to 7.9 in a nitrogen atmosphere, 29.2 g (0.162 mole) of D-α-methyl-β-acetylthiopropionyl chloride was added dropwise over about 1 hour at 2–5° C. with an agitation power of about 1.5 KW/m$^3$. After completion of dropwise addition, the ripening reaction was carried out under the same conditions for about 2 hours. This reaction mixture was adjusted to pH 7 by dropwise addition of 35 wt. % aqueous solution of HCl in a nitrogen atmosphere at about 1° C. Then, at an internal temperature of about 20° C. and under strong agitation, the mixture was acidified with 35 wt. % aqueous solution of HCl to cause crystallization in a nitrogen atmosphere. The 35 wt. % aqueous solution of HCl was added rapidly down to pH 5 and, thereafter, dropwise at a decreasing rate of about 0.2 pH unit, at 15-minute intervals down to pH 3 so as to cause crystallization gradually. Then, the dropping rate was gradually increased until a final pH value of 1.5 had been attained. The system was cooled gradually down to about 10° C. and mild stirring was continued for about 2 hours. The crystal crop was harvested by filtration, drained well, rinsed with about 60 ml of cold water, and sufficiently drained to provide 40.0 g of wet crystals (water content 16.0 %) of N-(D-α-methyl-β-acetylthiopropionyl)-L-proline (yield 80%; compound (3) (n=2) content=0.3 wt. %, compound (4) not detected).

EXAMPLE 3

Preparation of N-(D-α-methyl-β-acetylthiopropionyl)-L-proline with Low contents of Compound (3) and Compound (4)

To 100 g of deionized water were added 19.0 g (0.165 mole) of L-proline and 37.4 g (0.374 mole) of potassium hydrogen carbonate, followed by cooling to an internal temperature of about −3 to 0° C. Then, under stirring at an internal temperature of −3 to 0° C. in a nitrogen atmosphere, 29.2 g (0.162 mole) of D-α-methyl-β-acetylthiopropionyl chloride was added dropwise over about 4 hours. After completion of dropwise addition, the ripening reaction was continued under the same conditions for about 1 hour. The pH of the reaction mixture varied between 7.4 and 8.8 in the course of reaction. This reaction mixture was adjusted to pH 7 by adding 35 wt. % aqueous solution of HCl dropwise in a nitrogen atmosphere at about 1° C. Then, at an internal temperature of about 20° C. and under strong agitation, the mixture was acidified with 35 wt. % aqueous solution of HCl to cause crystallization in a nitrogen atmosphere. Thirty five wt. % aqueous solution of HCl was added rapidly down to pH 5 and, thereafter, dropwise at a decreasing rate of about 0.2 pH unit at 15-minute intervals down to pH 3 so as to cause crystallization gradually. Then, the dropping rate was gradually increased until a final pH value of 1.5 had been attained. The system was cooled gradually down to about 10° C. and mild agitation was continued for about 2 hours. The crystal crop was harvested by filtration, drained well, rinsed with about 60 ml of cold water, and sufficiently drained to provide 39.1 g of wet crystals (water content 14.0%) of N-(D-α-methyl-β-acetylthiopropionyl)-L-proline (yield 80%; compound (3) (n=2), compound (4) not detected.

EXAMPLE 4

Preparation of N-(D-α-methyl-β-acetylthiopropionyl)-L-proline with Low Contents of Compound (3) and Compound (4)

To 255 g of deionized water was added 57.0 g (0.495 mole) of L-proline and the mixture was cooled to about 5° C. Under stirring, 30 wt. % aqueous solution of NaOH was added slowly dropwise to adjust the mixture to pH 11.3 at about 0–3° C. Then, with the mixture being held at pH 11.0 to 11.5 in a nitrogen atmosphere, 87.6 g (0.485 mole) of D-α-methyl-β-acetylthiopropionyl chloride was added dropwise over about 1 hour at 2–5° C. with an agitation power of about 1.5 KW/m$^3$. After completion of dropwise addition, the ripening reaction was carried out under the same conditions for about 2 hours.

This reaction mixture was adjusted to pH 7 by dropwise addition of 35 wt. % aqueous solution of HCl in a nitrogen atmosphere at about 1° C. Then, at an internal temperature of about 60° C. and under strong agitation, the mixture was acidified with 35 wt. % aqueous solution of HCl to cause crystallization in a nitrogen atmosphere. Thirty five wt. % aqueous solution of HCl was added rapidly down to pH 5 and, thereafter, dropwise at a decreasing rate of about 0.2 pH unit at 15-minute intervals down to pH 3 so as to cause crystallization gradually. Then, the dropping rate was gradually increased until a final pH value of 1.5 had been attained. The system was cooled gradually down to about 10° C. and mild agitation was continued for about 2 hours. The resulting crystal crop was harvested by filtration, drained well, rinsed with about 180 ml of cold water, and sufficiently drained to provide 130.2 g of wet crystals (water content 15.0%) of N-(D-α-methyl-β-acetylthiopropionyl)-L-proline (yield 88%; compound (3) (n=2) content=0.4 wt. %, compound (4) not detected).

EXAMPLE 5

Preparation of N-(D-α-methyl-β-acetylthiopropionyl)-L-proline with Low Contents of Compound (3) and Compound (4)

To 85 g of deionized water was added 19.0 g (0.165 mole) of L-proline and the mixture was cooled to about 5° C. Under stirring, 30 wt. % aqueous solution of NaOH was added slowly dropwise to adjust the mixture to pH 11.3 at about 0–3° C. Then, with the mixture being maintained at pH 11.0 to 11.5 in a nitrogen atmosphere, 29.2 g (0.162 mole) of D-α-methyl-β-acetylthiopropionyl chloride was added dropwise over about 1 hour at 2–5° C. with an agitation power of about 1.5 KW/m$^3$. After completion of dropwise addition, the ripening reaction was carried out under the same conditions for about 2 hours.

This reaction mixture was adjusted to pH 7 by dropwise addition of 35 wt. % aqueous solution of HCl in a nitrogen atmosphere at about 1° C. To this solution was added 15.0 g of activated carbon and the mixture was stirred in a nitrogen atmosphere at about 20° C. for 1 lour. The carbon was then filtered off and the filtrate was washed with about 50 ml of deionized water. Then, at an internal temperature of about 20° C. and under strong agitation, the mixture was acidified with 35 wt. % aqueous solution of HCl to cause crystallization in a nitrogen atmosphere. Thirty five wt. % aqueous solution of HCl was added rapidly down to pH 5 and, thereafter, dropwise at a decreasing rate of about 0.2 pH unit at 15-minute intervals down to pH 3 so as to cause crystallization gradually. Then, the dropping rate was gradually increased until a final pH value of 1.5 had been attained. The system was cooled gradually down to about 10° C. and mild agitation was continued for about 2 hours. The crystal crop was harvested by filtration, drained well, rinsed with about 60 ml of cold water, and sufficiently drained to provide 43.0 g of wet crystals (water content 13.0%) of N-(D-α-methyl-β-acetylthiopropionyl)-L-proline (yield 89%; compound (3) (n=2) content=0.3 wt. %, compound (4) not detected).

EXAMPLE 6

Preparation of N-(D-α-methyl-β-acetylthiopropionyl)-L-proline with Low Contents of Compound (3) and Compound (4)

To 255 g of deionized water was added 57.0 g (0.495 mole) of L-proline and the mixture was cooled to about 5° C. Under stirring, 30 wt. % aqueous solution of NaOH was added slowly dropwise to adjust the mixture to pH 7.6 at about 0–3° C. Then, with the mixture being maintained at pH 7.4 to 7.9 in a nitrogen atmosphere, 87.6 g (0.485 mole) of D-α-methyl-β-acetylthiopropionyl chloride was added dropwise over about 1 hour at 2–5° C. with an agitation power of about 1.5 KW/m$^3$. After completion of dropwise addition, the ripening reaction was carried out under the same conditions for about 2 hours.

This reaction mixture was adjusted to pH 7 by dropwise addition of 35 wt. % aqueous solution of HCl in a nitrogen atmosphere at about 1° C. Then, at an internal temperature of about 60° C. and under strong agitation, the mixture was acidified with 35 wt. % aqueous solution of HCl to cause crystallization in a nitrogen atmosphere. Thirty five wt. % aqueous solution of HCl was added rapidly down to pH 5 and, thereafter, dropwise at a decreasing rate of about 0.2 pH unit at 15-minute intervals down to pH 3 so as to cause crystallization gradually. Then, the dropping rate was gradually increased until a final pH value of 1.5 had been attained. The system was cooled gradually down to about 10° C. and mild agitation was continued for about 2 hours. The resulting crystal crop was harvested by filtration, drained well, rinsed with about 180 ml of cold water, and sufficiently drained to provide 114.3 g of wet crystals (water content 12%) of N-(D-α-methyl-β-acetylthiopropionyl)-L-proline (yield 80%; compound (3) (n=2) content<0.1 wt. %, compound (4) not detected).

Among the N-(D-α-methyl-β-acetylthiopropionyl)-L-proline products obtained above in Examples 1–6, there was no difference in the amount of impurity other than compound (3) and compound (4).

Moreover, in any of Examples 1–6, the proportions of compounds (3) wherein n=3 and n=4 were negligible as compared with compound (3) wherein n=2.

EXAMPLE 7

Preparation of Captopril

The wet crystals containing 37.4 g of N-(D-α-methyl-β-acetylthiopropionyl)-L-proline (0.144 mole; compound (3) (n=2) content 3.7 wt. %, compound (4) content 0.1 wt. %) as obtained in Example 1 were added to 60 g of deionized water and the mixture was adjusted to pH not over 0 by adding 22.6 g of 35 wt. % aqueous solution of HCl at an internal temperature of about 70° C. in the air and stirred for 6 hours (the pH after 6 hours of agitation was still not over 0). After cooling to an internal temperature of about 40° C., sodium chloride was added up to substantial saturation and the mixture was stirred for about 1 hour. Then, in the air and at an internal temperature of about 40° C., 48 wt. % aqueous solution of NaOH was added slowly dropwise so as to adjust the mixture to pH 1.5. After cooling to an internal temperature of about 30° C., seed crystals were added for crystallization. After 30 minutes of strong stirring under the same conditions, the mixture was cooled to 4° C. while its pH was maintained at 1.5 by adding 35 wt. % aqueous solution of HCl dropwise. The internal temperature was further lowered to about 1° C. and the mixture was kept under strong agitation for 30 minutes. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.5 g (0.127 mole) of captopril. The yield based on N-(D-α-methyl-β-acetylthiopropionyl)-L-proline was 88 mole %.

The quality characteristics of the captopril thus obtained were as follows.

White crystals, substantially odorless.

$[\alpha]_D^{25}$=−1280 (c=1.0, EtOH, 100 mm)

HPLC purity: 99.5 wt. %

Assay by titration: 99.4%

Disulfide content: 0.2 wt. %

β-Mercapto-α-methylpropionic acid content: <0.1 wt. %

N-(α-methyl-β-(β-methyl-β-hydroxycarbonyl)ethylthiopropionyl)-L-proline content: 0.2 wt. %

N-acetyl-L-proline content: <0.1 wt. %

COMPARATIVE EXAMPLE 1

Preparation of Captopril

The wet crystals containing 37.4 g of N-(D-α-methyl-β-acetylthiopropionyl)-L-proline (0.144 mole; compound (3) (n=2) content 3.7 wt. %, compound (4) content 0.1 wt. %) as obtained in Example 1 were added to 51 g of deionized water. Then, in the air and at an internal temperature of about 20° C., 55.2 g of 30 wt. % aqueous solution of NaOH was added dropwise over about 4 hours. The mixture was stirred under the same conditions for 1 hour. Then, the mixture was adjusted to pH 6 by adding 35 wt. % aqueous solution of HCl at an internal temperature of 20–25° C. in the air. At an internal temperature of about 30° C., sodium chloride was added up to substantial saturation and the mixture was stirred for about 1 hour. After heating the system to an internal temperature of about 40° C., 35 wt. % aqueous solution of HCl was added slowly dropwise so as to adjust the mixture to pH 3.5. The mixture was subjected to about 1 hour of strong agitation to cause crystallization. Then, in the air and at an internal temperature of about 40° C., 35 wt. % aqueous solution of HCl was added dropwise over not less than 1 hour to adjust the mixture down to pH 3.0, followed by about 1 hour of strong stirring. Then, under the same conditions, 35 wt. % aqueous solution of HCl was further added dropwise over about 1 hour to bring the pH to 1.5. The mixture was further subjected to strong stirring for 30 minutes and, then, cooled to an internal temperature of about 1° C. The mixture was held under the same conditions for 30 minutes. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.6 g (0.127 mole) of captopril. The yield based on N-(D-α-methyl-β-acetylthiopropionyl)-L-proline was 88 mole %.

The quality characteristics of the captopril thus obtained were as follows.

White crystals, substantially odorless.

$[\alpha]_D^{25}$=−128° (c=1.0, EtOH, 100 mm)

HPLC purity: 95.5 wt. %

Assay by titration: 95.4%

Disulfide content: 2.5 wt. %

α-Mercapto-β-methylpropionic acid content: <0.1 wt. %

N-(α-methyl-β-(β-methyl-β-hydroxycarbonyl)ethylthiopropionyl)-L-proline content: 1.6 wt. %

N-acetyl-L-proline content: <0.1 wt. %

EXAMPLE 8

Preparation of Captopril

The wet crystals containing 37.4 g of N-(D-α-methyl-β-acetylthiopropionyl)-L-proline (0.144 mole; compound (3) (n=2) content 3.7 wt. %, compound (4) content 0.1 wt. %) as obtained in Example 1 were added to 60 g of deionized water and the mixture was adjusted to pH not over 0 by adding 22.6 g of 35 wt. % aqueous solution of HCl at an internal temperature of about 70° C. and stirred in a nitrogen atmosphere for 6 hours (the pH after 6 hours of agitation was still not over 0). After cooling to an internal temperature of about 40° C., sodium chloride was added up to substantial saturation and the mixture was stirred for about 1 hour. Then, in a nitrogen atmosphere and at an internal temperature of about 40° C., 48 wt. % aqueous solution of NaOH was added slowly dropwise so as to adjust the mixture to pH 1.5. After cooling to an internal temperature of about 30° C., seed crystals were added for crystallization. After 30 minutes of strong stirring under the same conditions, the mixture was cooled to 4° C. while its pH was maintained at 1.5 by adding 35 wt. % aqueous solution of HCl dropwise. The internal temperature was further lowered to about 1° C. and the mixture was kept under strong agitation for 30 minutes. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.5 g (0.127 mole) of captopril. The yield based on N-(D-α-methyl-β-acetylthiopropionyl)-L-proline was 88 mole %.

The quality characteristics of the captopril thus obtained were as follows.

White crystals, substantially odorless.
$[\alpha]_D^{25} = -1280$ (c=1.0, EtOH, 100 mm)
HPLC purity: 99.7 wt. %
Assay by titration: 99.7%
Disulfide content: <0.1 wt. %
α-Mercapto-β-methylpropionic acid content: <0.1 wt. %
N-(α-methyl-β-(β-methyl-β-hydroxycarbonyl)ethylthiopropionyl)-L-proline content: 0.2 wt. %
N-acetyl-L-proline content: <0.1 wt. %

EXAMPLE 9

Preparation of Captopril

The wet crystals containing 37.4 g of N-(D-α-methyl-β-acetylthiopropionyl)-L-proline (0.144 mole; compound (3) (n=2) content 0.4 wt. %) as obtained in Example 4 were added to 60 g of deionized water and the mixture was adjusted to pH not over 0 by adding 22.6 g of 35 wt. % aqueous solution of HCl at an internal temperature of about 70° C. and stirred in a nitrogen atmosphere for 6 hours (the pH after 6 hours of agitation was still not over 0). After cooling to an internal temperature of about 40° C., sodium chloride was added up to substantial saturation and the mixture was stirred for about 1 hour. Then, in a nitrogen atmosphere and at an internal temperature of about 40° C., 48 wt. % aqueous solution of NaOH was added slowly dropwise so as to adjust the mixture to pH 1.5. After cooling to an internal temperature of about 30° C., seed crystals were added for crystallization. After 30 minutes of strong stirring under the same conditions, the mixture was cooled to 4° C. while its pH was maintained at 1.5 by adding 35 wt. % aqueous solution of HCl dropwise. The internal temperature was further lowered to about 1° C. and the mixture was kept under strong agitation for 30 minutes. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.5 g (0.127 mole) of captopril. The yield based on N-(D-α-methyl-β-acetylthiopropionyl)-L-proline was 88 mole %.

The quality characteristics of the captopril thus obtained were as follows.

White crystals, substantially odorless.
$[\alpha]_D^{25} = -128°$ (c=1.0, EtOH, 100 mm)
HPLC purity: 99.8 wt. %
Assay by titration: 99.8%
Disulfide content: <0.1 wt. %
α-Mercapto-β-methylpropionic acid content: <0.1 wt. %
N-(α-methyl-β-(β-methyl-β-hydroxycarbonyl)ethylthiopropionyl)-L-proline content: <0.1 wt. %
N-acetyl-L-proline content: <0.1 wt. %

EXAMPLE 10

Preparation of Captopril

The wet crystals containing 37.4 g of N-(D-α-methyl-β-acetylthiopropionyl)-L-proline (0.144 mole; compound (3) (n=2) content 0.4 wt. %) as obtained in Example 4 were added to 60 g of deionized water. In a nitrogen atmosphere and at an internal temperature of about 80° C., the mixture was adjusted to pH not over 0 by adding 7.5 g of 35 wt. % aqueous solution of HCl and stirred for 10 hours (the pH after 10 hours of agitation was still not over 0). The mixture was then cooled to an internal temperature of about 20° C., and in a nitrogen atmosphere and at an internal temperature of 20–25° C., 48 wt. % aqueous solution of NaOH was added dropwise to adjust the mixture to pH 13.5. The mixture was further stirred under the same conditions for 1 hour. Then, in a nitrogen atmosphere and at an internal temperature of 20 to 25° C., 35 wt. % aqueous solution of HCl was added dropwise to adjust the mixture to pH 6. Then, at an internal temperature of about 30° C., sodium chloride was added up to substantial saturation and the mixture was stirred for about 1 hour. After the system was heated to an internal temperature of about 40° C., 35 wt. % aqueous solution of HCl was added slowly dropwise to adjust the mixture to pH 3.5. This mixture was further subjected to strong stirring for about 1 hour to cause crystallization. Then, at an internal temperature of 40° C., 35 wt. % aqueous solution of HCl was further added dropwise over not less than 1 hour to bring the pH to 3.0 and the mixture was further stirred vigorously for about 1 hour. Then, at an internal temperature of 40° C., 35%: aqueous solution of HCl was further added dropwise over about 1 hour to adjust the mixture to pH 1.5. The mixture was further stirred vigorously for 30 minutes, after which time it was cooled to an internal temperature of about 1° C. The mixture was held under the same conditions for 4 hours. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.2 g (0.125 mole) of captopril. The yield based on N-(D-α-methyl-β-acetylthiopropionyl)-L-proline was 87 mole %.

The quality characteristics of the captopril thus obtained were as follows.

White crystals, substantially odorless.
$[\alpha]_D^{25} = -128°$ (c=1.0, EtOH, 100 mm)
HPLC purity: 99.9 wt. %
Assay by titration: 99.9%
Disulfide content: <0.1 wt. %
α-Mercapto-β-methylpropionic acid content: <0.1 wt. %
N-(α-methyl-β-(β-methyl-β-hydroxycarbonyl)ethylthiopropionyl)-L-proline content: <0.1 wt. %
N-acetyl-L-proline content: <0.1 wt. %

EXAMPLE 11

Preparation of Captopril

The wet crystals containing 37.4 g of N-(D-α-methyl-β-acetylthiopropionyl)-L-proline (0.144 mole; compound (3) (n=2) content<0.1 wt. %) as obtained in Example 6 were added to 60 g of deionized water. In a nitrogen atmosphere and at an internal temperature of about 90° C., the mixture was adjusted to pH not over 0 by adding 4.5 g of 35 wt. % aqueous solution of HCl and stirred for 10 hours (the pH after 10 hours of agitation was 0.3). The mixture was then cooled to an internal temperature of about 20° C., and in a nitrogen atmosphere and at an internal temperature of 20–25° C., 48 wt. % aqueous solution of NaOH was added dropwise to adjust the mixture to pH 5. Then, at an internal temperature of about 30° C., sodium chloride was added up to substantial saturation and the mixture was stirred for about 1 hour. Thirty five wt. % aqueous solution of HCl was added slowly dropwise to adjust the mixture to pH 3.5. This mixture was further subjected to strong stirring for about 1 hour to cause crystallization. Then, at an internal temperature of about 30° C., 35 wt. % aqueous solution of HCl was further added dropwise over not less than 1 hour to bring the pH to 3.0 and the mixture was further stirred vigorously for about 1 hour.

Then, at an internal temperature of about 30° C., 35 wt. % aqueous solution of HCl was further added dropwise over about 1 hour to adjust the mixture to pH 1.5. The mixture was further stirred vigorously for 30 minutes, after which time it was cooled to an internal temperature of about 1° C. The mixture was held under the same conditions for 4 hours. Thereafter, the crystals deposited were collected by filtration, drained well, rinsed with about 15 ml of cold water twice, and sufficiently drained. The wet crystals thus obtained were dried in vacuo (the degree of vacuum: 1–5 mmHg) at a temperature not over 40° C. to provide 27.4 g (0.126 mole) of captopril. The yield based on N-(D-α-methyl-β-acetylthiopropionyl)-L-proline was 88 mole %.

The quality characteristics of the captopril thus obtained were as follows.

White crystals, substantially odorless.
$[\alpha]_D^{25} = -128°$ (c=1.0, EtOH, 100 mm)
HPLC purity: 99.8 wt. %
Assay by titration: 99.8%
Disulfide content: <0.1 wt. %
α-Mercapto-β-methylpropionic acid content: <0.1 wt. %
N-(α-methyl-β-(β-methyl-β-hydroxycarbonyl)ethylthiopropionyl)-L-proline content: not detected
N-acetyl-L-proline content: <0.1 wt. %

EXAMPLE 12

Preparation of Captopril

The wet crystals containing 37.4 g of N-(D-α-methyl-β-acetylthiopropionyl)-L-proline (0.144 mole; compound (3) (n=2) content <0.1 wt. %) as obtained in Example 6 were added to 60 g of deionized water. In a nitrogen atmosphere and at an internal temperature of about 70° C., the mixture was adjusted to pH not over 0 by adding 22.6 g of 35 wt. % aqueous solution of HCl and stirred for 6 hours (the pH after 6 hours of agitation was still not over 0). The mixture was then cooled to an internal temperature of about 20° C., and in a nitrogen atmosphere and at an internal temperature of 20–25° C., 48 wt. % aqueous solution of NaOH was added dropwise to adjust the mixture to pH 2. Then, at an internal temperature of about 30° C., sodium chloride was added up to substantial saturation and the mixture was stirred for about 1 hour. To this mixture was added 300 ml of tert-butyl acetate, and after 30 minutes of strong stirring at an internal temperature of about 20° C., the agitation was stopped to leave the mixture standing for 30 minutes. The organic layer was separated from the aqueous layer. To the aqueous layer was added 300 ml of tert-butyl acetate and the mixture was stirred vigorously at an internal temperature of about 20° C. for 30 minutes. The agitation was then stopped to leave the mixture standing for 30 minutes. The organic layer was separated from the aqueous layer. The organic layers were combined, mixed with 30 ml of deionized water, and subjected to 30 minutes of strong stirring. The agitation was stopped to leave the mixture standing for 30 minutes. The organic layer was separated from the aqueous layer and dehydrated over anhydrous sodium sulfate. After the sodium sulfate was filtered off, the filtrate was concentrated under reduced pressure to 100 g, whereby crystallization was occurred. The resulting slurry was cooled to an internal temperature of about 1° C. under agitation and allowed to stand under the same conditions for 4 hours. Thereafter, the crystals deposited were collected by filtration, drained well, rinsed with 15 ml of cold tert-butyl acetate twice, and sufficiently drained. The wet crystals thus obtained were dried in vacuo (the degree of vacuum: 1–5 mmHg) at a temperature not over 40° C. to provide 26.9 g (0.123 mole) of captopril. The yield based on N-(D-α-methyl-β-acetylthiopropionyl)-L-proline was 86 mole %.

The quality characteristics of the captopril thus obtained were as follows.

White crystals, substantially odorless.
$[\alpha]_D^{25} = -128°$ (c=1.0, EtOH, 100 mm)
HPLC purity: 99.8 wt. %
Assay by titration: 99.8%
Disulfide content: <0.1 wt. %
α-Mercapto-β-methylpropionic acid content: <0.1 wt. %
N-(α-methyl-β-(β-methyl-β-hydroxycarbonyl)ethylthiopropionyl)-L-proline content: not detected
N-acetyl-L-proline content: <0.1 wt. %

INDUSTRIAL APPRICABILITY

According to the present invention described above, high-quality captopril can be produced in good yield and at low cost through inhibition of formation of contaminant byproducts which could hardly be removed by purification.

We claim:

1. A process for producing captopril of the following formula (1)

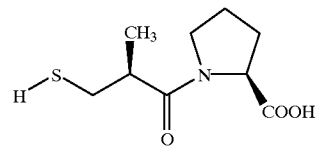

(1)

comprising subjecting a substrate compound of the following formula (2)

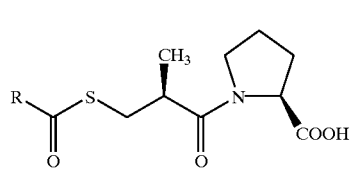

(2)

wherein R represents alkyl or alkoxy, to hydrolysis reaction in aqueous medium to remove RCO group and isolating, said hydrolysis reaction in aqueous medium being conducted in the presence of a strong acid at pH not over 1 and a reaction temperature not below 40° C.

2. The process for producing captopril according to claim 1 wherein the reaction temperature is 50 to 100° C.

3. The process for producing captopril according to claim 1 wherein the strong acid is hydrochloric acid.

4. The process for producing captopril according to claim 3 wherein hydrochloric acid is used in a proportion of not less than 0.1 molar equivalent based on the substrate compound of formula (2).

5. The process for producing captopril according to claim 1, wherein said isolation comprises crystallization from aqueous medium at pH not over 3 and a temperature not higher than 50° C.

6. The process for producing captopril according to claim 1, wherein said isolation comprises extraction with an acetic acid ester at pH not over 3 in aqueous medium with or without subsequent crystallization.

7. The process for producing captopril according to claim 5 wherein said isolation is carried out at a temperature not exceeding 5° C.

8. The process for producing captopril according to claim 5 wherein said isolation is preceded by adjusting the aqueous medium after said hydrolysis reaction to pH not below 12, holding it at about 0 to 50° C. for not less than 1 minute, and readjusting it to pH not over 3.

9. The process for producing captopril according to claim 1, wherein said isolation comprises bringing the inorganic salt concentration of the aqueous medium to saturation to thereby lower the solubility of captopril.

10. The process for producing captopril according to claim 1, which is carried out in an inert atmosphere.

11. The process for producing captopril according to claim 1, wherein said substrate compound of general formula (2) contains, as impurity, at least one of a compound of the following formula (3)

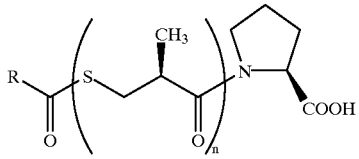

(3)

wherein R represents alkyl or alkoxy; n represents an integer of 2 to 4, and a compound of the following formula (4)

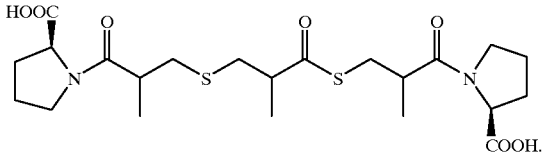

(4)

12. The process for producing captopril according to claim 1, wherein said substrate compound of formula (2) is a compound obtained by subjecting an acid halide of the following formula (5)

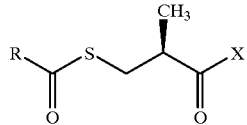

(5)

wherein R represents alkyl or alkoxy; X represents halogen, and L-proline of the following formula (6)

(6)

to Schotten-Baumann reaction under basic conditions.

13. The process for producing captopril according to claim 12 wherein the Schotten-Baumann reaction is conducted in accordance with the following (A) or (B):
  (A) the Schotten-Baumann reaction of said acid halide of formula (5) with L-proline of formula (6) in the presence of a deacidifying condensing agent in a basic aqueous medium is conducted at pH 7 to 10 and a reaction temperature not over 10° C. to thereby suppress by-production of said compound of formula (3) and/or said compound of formula (4);
  (B) the Schotten-Baumann reaction of said acid halide of formula (5) with L-proline of formula (6) in the presence of a deacidifying condensing agent in a basic aqueous medium is conducted by using potassium hydrogen carbonate as the deacidifying, condensing agent to thereby suppress by-production of said compound of formula (3) and/or said compound of formula (4).

14. The process for producing captopril according to claim 1 wherein the aqueous medium consists essentially of water.

15. The process for producing captopril according to claim 12, wherein after the Schotten-Baumann reaction and before the hydrolysis reaction, the purification is conducted in accordance with the following procedure (C) and/or (D), to remove the concomitant compound of formula (3) and/or of formula (4):
  (C) the substrate compound of formula (2) is caused to crystallize out from the aqueous medium containing said substrate compound at 35 to 100° C. under acidic conditions to thereby remove the concomitant compound of formula (3) and/or compound of formula (4):
  (D) the aqueous medium containing the substrate compound of formula (2) is treated with activated carbon at pH not over 12.

16. The process for producing captopril according to claim 13, wherein after the Schotten-Baumann reaction and before the hydrolysis reaction, the purification is conducted in accordance with the following procedure (C) and/or (D), to remove the concomitant compound of formula (3) and/or of formula (4):
  (C) the substrate compound of formula (2) is caused to crystallize out from the aqueous medium containing said substrate compound at 35 to 100° C. under acidic conditions to thereby remove the concomitant compound of formula (3) and/or compound of formula (4):
  (D) the aqueous medium containing the substrate compound of formula (2) is treated with activated carbon at pH not over 12.

17. The process for producing captopril according to claim 13 wherein the aqueous medium consists essentially of water.

18. The process for producing captopril according to claim 15 wherein the aqueous medium consists essentially of water.

19. The process for producing captopril according to claim 16 wherein the aqueous medium consists essentially of water.

20. The process for producing captopril according to claim 2 wherein the strong acid is hydrochloric acid.

21. The process for producing captopril according to claim 2 wherein said isolation comprises crystallization from aqueous medium at pH not over 3 and a temperature not higher than 50° C.

22. The process for producing captopril according to claim 3 wherein said isolation comprises crystallization from aqueous medium at pH not over 3 and a temperature not higher than 50° C.

23. The process for producing captopril according to claim 4 wherein said isolation comprises crystallization from aqueous medium at pH not over 3 and a temperature not higher than 50° C.

24. The process for producing captopril according to claim 2 wherein said isolation comprises extraction with an acetic acid ester at pH not over 3 in aqueous medium with or without subsequent crystallization.

25. The process for producing captopril according to claim 3 wherein said isolation comprises extraction with an acetic acid ester at pH not over 3 in aqueous medium with or without subsequent crystallization.

* * * * *